United States Patent [19]

Fahim

[11] 4,078,556

[45] Mar. 14, 1978

[54] APPARATUS USEFUL IN SUPPRESSION OF SPERMATOGENESIS

[76] Inventor: Mostafa S. Fahim, 500 Hulen Dr., Columbia, Mo. 65201

[21] Appl. No.: 674,111

[22] Filed: Apr. 6, 1976

[51] Int. Cl.² .................. A61H 19/00; A61F 7/00
[52] U.S. Cl. ................... 128/24 A; 128/402
[58] Field of Search ............ 128/24 A, 24.1, 362, 128/399, 400, 402, 412, DIG. 2

[56] References Cited

U.S. PATENT DOCUMENTS

| | | | |
|---|---|---|---|
| 2,970,073 | 1/1961 | Prange | 128/24 A |
| 3,325,976 | 6/1967 | West | 128/DIG. 2 UX |
| 3,371,660 | 3/1968 | Carlin | 128/24 A X |
| 3,499,437 | 3/1970 | Balamuth | 128/24 A |
| 3,867,929 | 2/1975 | Joyner et al. | 128/24 A X |

FOREIGN PATENT DOCUMENTS 824,683 3/1951 Germany .................. 128/24 A

OTHER PUBLICATIONS

Fahim et al., "Heat in Male Contraception", Contraception, vol. 11, No. 5, May 1975, pp. 549–562.

Primary Examiner—Robert W. Michell
Assistant Examiner—Lee S. Cohen
Attorney, Agent, or Firm—Grace J. Fishel

[57] ABSTRACT

Apparatus useful in suppressing spermatogenesis in human males by applying ultrasonic vibrations to the testes. More particularly, apparatus useful in suppressing spermatogenesis by sonicating male testes including a cup for immersing the testes in an ultrasonic coupling agent and an ultrasonic applicator for applying ultrasonic vibrations thereto.

9 Claims, 11 Drawing Figures

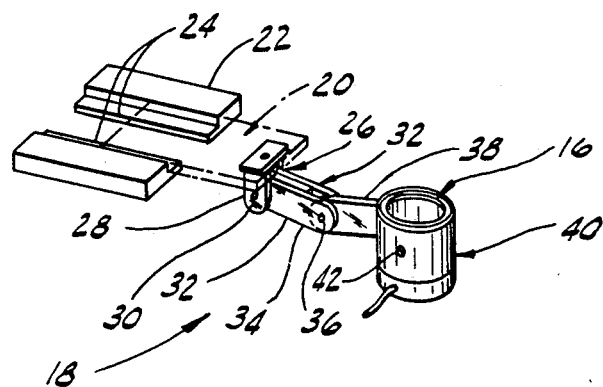
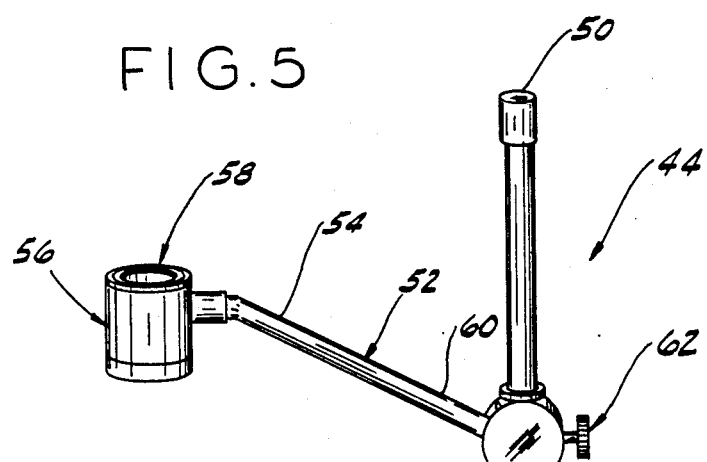
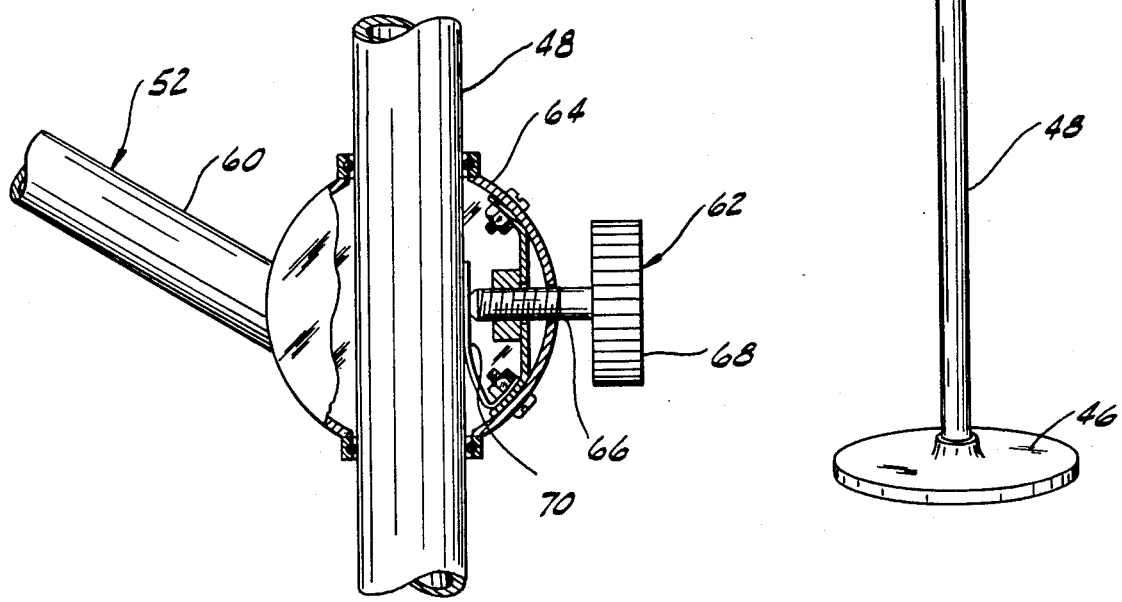

APPARATUS USEFUL IN SUPPRESSION OF SPERMATOGENESIS

This invention relates to apparatus useful in the suppression of spermatogenesis in human males with ultrasound.

Recently, there has been increasing interest in developing a male contraceptive. Ideally such a contraceptive would cause temporary or permanent sterility selectively as desired without affecting a man's sex drive, his sex characteristics or general health. Spurring this interest has been a growing concern over population growth, coupled with fears that long-term use of birth control pills or intrauterine devices may be harmful to some women.

Despite some progress, development of a male antifertility agent has been slow. Presently, the most promising pharmaceutical approach to a temporary male contraceptive combines synthetic testosterone with an analogue called danazol. At the most effective dosage, sperm production stops entirely or drops to a very low level but not without certain side effects. More particularly, testosterone sometimes causes a rise in blood fats which increases the risk of heart attack.

Up until now, vasectomy has been the only non-pharmaceutical male contraceptive other than condoms, which most couples reject as unreliable and cumbersome. A vasectomy is a surgical procedure which consists of cutting the tube which carries sperm from the testes to the penis and which requires skilled personnel and an anesthetic to perform. It is usually not reversible, is painful and involves the usual risks associated with surgery. This method is also frequently accompanied by complications such as hematomata, edema, pain on ejaculation, sperm granulomata and vas recanalization. It is also feared that vasectomy can produce certain adverse long-term effects.

More particularly, it has been found that vasectomy in male rats causes reduction in testis weight, reduction of testosterone in the blood, body weight gain and fat deposits and partial impairment of drug-metabolizing enzymes in the liver. Fed. Proc. Vol. 33, No. 3, March 1974. Since there have been no long-term studies on the effect of vasectomy on men, there is concern that humans may experience the same adverse effects as rats undergoing this procedure.

The ability of heat to suppress spermatogenesis has been known for many years. Researchers in 1922 were probably the first to suggest that the damage to the seminiferous epithelium of cryptorchid testes is the result of exposure of such testes to intra-abdominal temperature, which is higher than the intrascrotal temperature. J. Anat. 56:98. This suggestion has been supported by observations that intrascrotal testes exposed experimentally to elevated temperatures respond with rapid degeneration of the seminiferous epithelium. Japan Med. World 3:160–163 (1923), Am. J. Anat. 34:373–380 (1924) and J. Exp. Zool. 49:459–463 (1927).

While the effect of heat on the testes was generally known, it had not been considered for its contraceptive potential before the research of which the present invention is a portion. To this end, several sources of heat including hot water, infrared, microwavs and ultrasound were tried for their contraceptive potential on male rats. On the basis of these tests, it was found that infrared was more effective than hot water but less so than microwaves and ultrasound. Moreover, infrared treatment caused some skin drying and burning. Microwaves, on the other hand, unlike ultrasound, required elaborate shielding to protect against blinding and other tissue damage. Based on ease of treatment and effectiveness, ultrasound was found to be the preferred method of treatment. These tests were reported in Contraception, Vol. 11, No. 5, May 1975.

The effect of ultrasound on the testes of other laboratory animals has also ben tested with similar results to that in rats. These tests are reported in a paper presented to the American Fertility Society in April 1976.

In view of the above, among the several objects of the present invention may be noted the provision of apparatus useful in suppressing spermatogenesis in human males with ultrasound. This apparatus provides for the controlled application of ultrasonic vibrations to the testes of human males in such a way to cause temporary or permanent sterility selectively as desired without affecting the subject's sex drive, his sex characteristics or general health. Other objects and features will be in part apparent and in part pointed out hereinafter.

This invention accordingly comprises the apparatus hereinafter described, the scope of the invention being indicated in the subjoined claims.

In accordance with the present invention, apparatus for the treatment of the testes of human males with ultrasonic vibrations is provided. More particularly, apparatus for immersing the testes in an ultrasound coupling agent contained in a suitable vessel. The apparatus then provides for treatment of the immersed testes with ultrasonic vibrations from an ultrasonic applicator which is constructed so that it can be placed in direct contact with the coupling agent in the vessel or so that its vibrations are passed thereto through the walls of the vessel.

In the accompanying drawings, several embodiments of the apparatus of the invention are illustrated.

FIG. 4 is an enlarged perspective view of the adjustable holder for use in holding the cup during the application of ultrasound to human testes;

FIG. 5 is a perspective view of a stand for use in applying ultrasound to human testes;

FIG. 6 is a longitudinal cross-sectional view taken along line 6—6 in FIG. 5;

Figure 2:
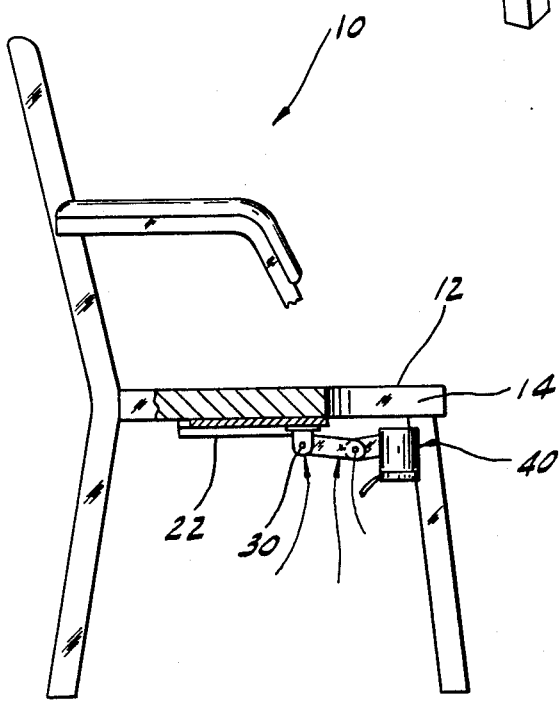
FIG. 2 is a side elevational view of the chair shown in FIG. 1; shown partly in section.
Figure 3:
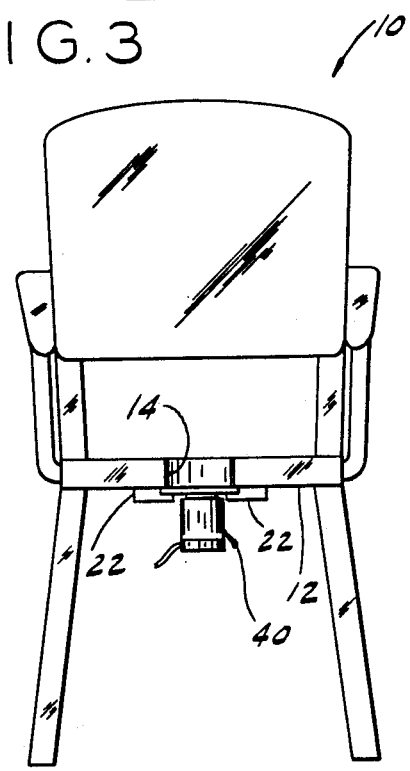
FIG. 3 is a front elevational view of the chair shown in FIG. 1.

Reference numeral 10 refers to a chair constructed according to the present invention, said chair having a seat 12 with an elongated U-shaped notch 14 in the front edge thereof. Notch 14 is centrally located along the front edge so that when a man is seated on chair 10 with his legs spread that his testicles hang freely through the notch. As best seen in FIG. 2, the testicles of the subject so positioned are received in cup 16 for treatment as hereinafter described.

Cup 16 is supported by a bracket assembly 18 which is mounted on a slidable drawer shelf 20. Shelf 20 is suported by strips 22 which are attached to the underside of seat 12. Strips 22 extend from adjacent the base of U-shaped notch 14 towards the back of seat 12 and are positioned generally parallel to the lateral edges of the notch.

Shelf 20 is wider than notch 14 and is received in opposing rabbeted lateral edges 24 of strips 22. Rabbets 24 are dimensioned so that shelf 20 is slidable therealong without unnecessary looseness. As shown, shelf 20 is longer than notch 14 so that shelf 20 may be extended beyond the leading edge of chair seat 12 as well as retracted beyond the bottom of notch 14.

Figure 1:
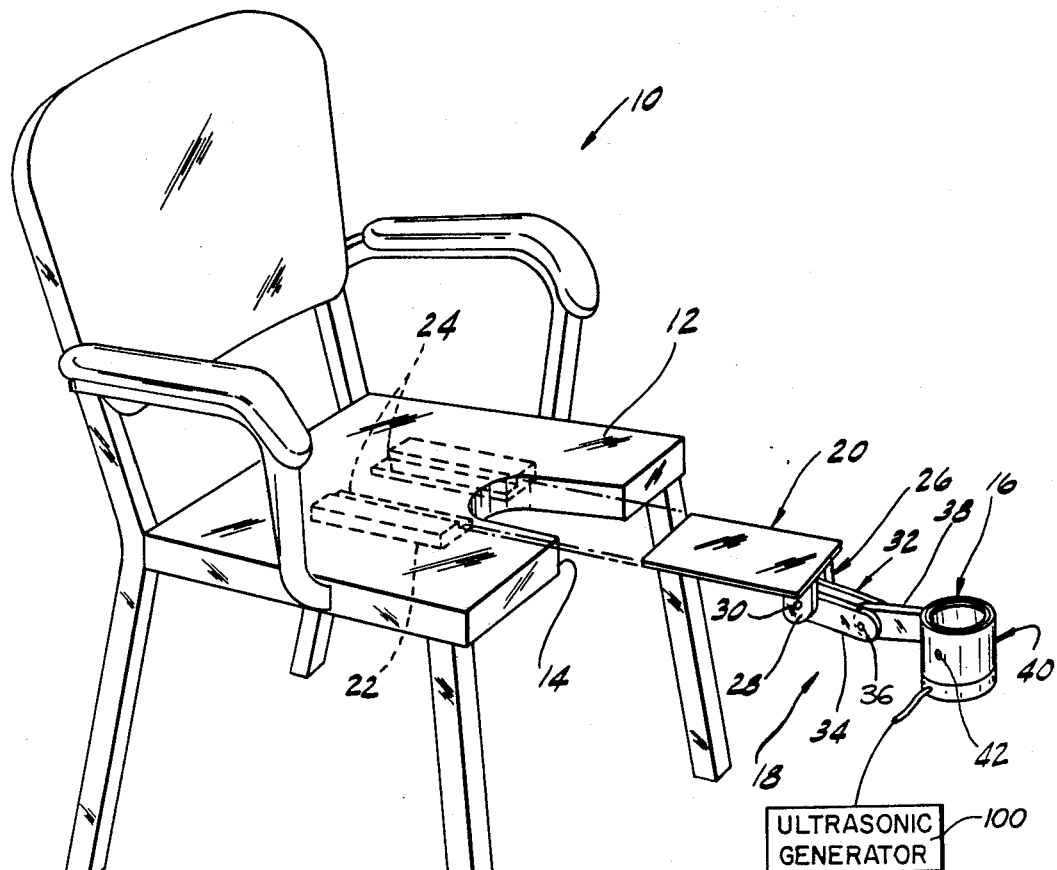
FIG. 1 is an exploded perspective view of a chair for use in applying ultrasound to human testes.

As best seen in FIG. 1, bracket assembly 18 is attached adjacent the leading edge of shelf 20 by linkage 26. Linkage 26 has two upstanding apertured ears 28 extending down from the underside of shelf 20 for pivotal attachment at 30 to linkage 32. Linkage 32 is like linkage 26 and includes two upstanding apertured ears 34 for pivotal attachment at 36 to apertured arm 38 of holder 40. Pivotal linkags 30 and 36 are adjusted so that bracket assembly 18 remains in a selected position once placed therein. Holder 40 is cylindrical in shape and is dimensioned to receive cup 16. It is provided with a set screw 42 to prevent cup 16 from being unseated therefrom.

As will be understod, bracket assembly 18 provides for vertical displacement of cup 16 from the plane of chair seat 12 and for maintaining the cup in level condition. Whereas, shelf 20 provides for displacement of cup 16 with respect to the leading edge of the seat. The chair so adjustable is adaptable to the anatomy of the particular patient.

Another embodiment of the present invention is shown in FIG. 5. In this figure, reference numeral 44 refers to a stand having a base 46 and an upstanding leg 48 attached thereto. As shown, leg 48 is tubular in cross-section and is tipped with a cap 50.

An arm 52 is adjustably attached to leg 48. The distal end 54 of arm 52 terminates in a holder 56 for cup 58. Holder 56 and cup 58 are similar in function to holder 40 and cup 16 and may be identical thereto. The proximal end 60 of arm 52 is received in a clamp 62. As best seen in FIG. 6, clamp 62 includes a ball-shaped housing 64 which is passed along its diameter over leg 48. Housing 64 is tapped to receive a threaded shaft 66 associated with handle 68. When shaft 66 is moved to the left, as viewed in FIG. 6, in response to movements of handle 68, the forward end of the shaft bears against spring biased member 70 which acts as a brake on leg 48. Spring biased member 70 is provided so that clamp 62 does not mar leg 48 when tightened thereon. As will be understood, clamp 62 provides for vertical displacement of cup 58 to adjust to the anatomy of the standing patient.

Cups 16 and 58 are preferably formed of methyl methacrylate or of similar material and are provided in a range of sizes. If three cups are provided as follows, it has been found that the testes of most subjects are accommodated: Cup A having an inside diameter of 4.9 cm and a depth of 4.5 cm, Cup B having an inside diameter of 6.9 cm and a depth of 5.5 cm and Cup C having an inside diameter of 8.2 cm and a depth of 5.8 cm. Cups 16 and 58 are preferably provided with a rubber cushion 71 around their rims.

Figure 7:
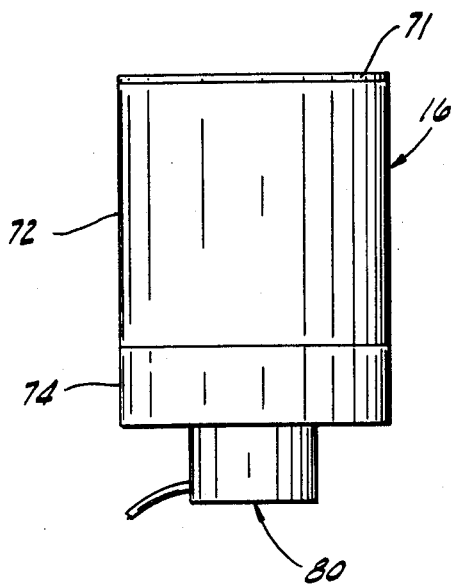
FIG. 7 is a side elevational view of a cup for use in applying ultrasound to human testes.
Figure 8:
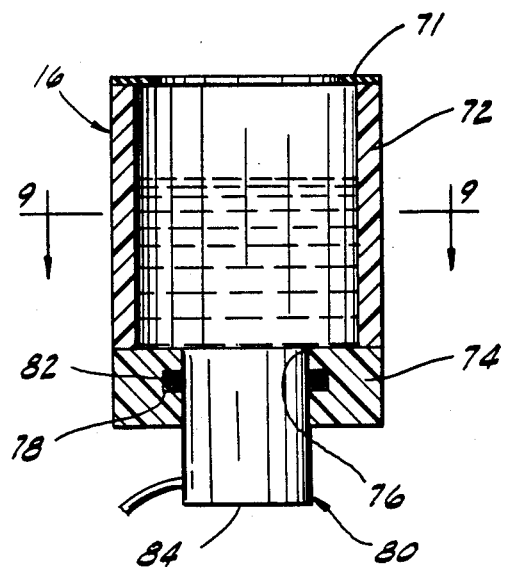
FIG. 8 is a longitudinal cross-sectional view taken along line 8—8 in FIG. 9.
Figure 9:
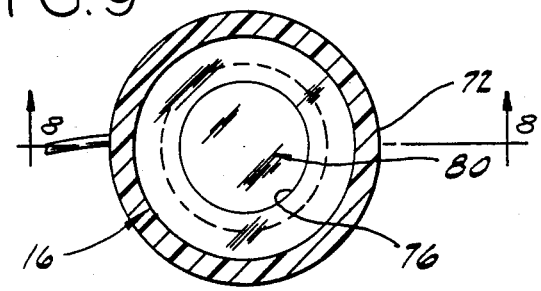
FIG. 9 is a horizontal cross-section view taken along line 9—9 in FIG. 8.

As shown in FIGS. 7-9, cup 16 includes a cylindrical sidewall 72 which is sealed on one end to a bottom wall 74. Bottom wall 74 has an aperture 76 centrally located therein, said aperture having a recess 78 in the rim thereof. An ultrasound applicator 80 is sealed in aperture 76 with an O-ring 82 which is fitted in recess 78 provided therefor. Ultrasound applicator 80 includes a transducer (not shown) within a housing 84 which protects the transducer from the contents of cup 16.

Figure 10:
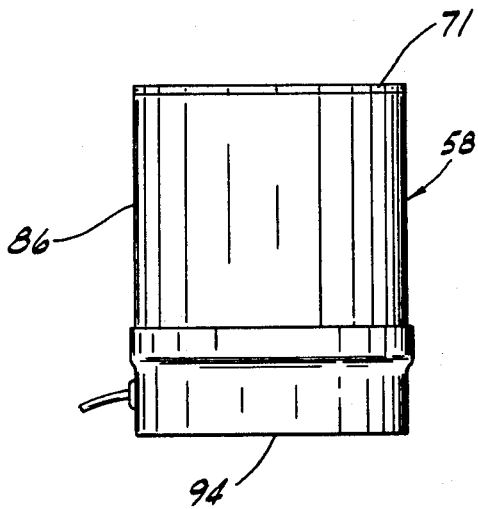
FIG. 10 is a side elevational view of another cup for use in applying ultrasound to human testes.
Figure 11:
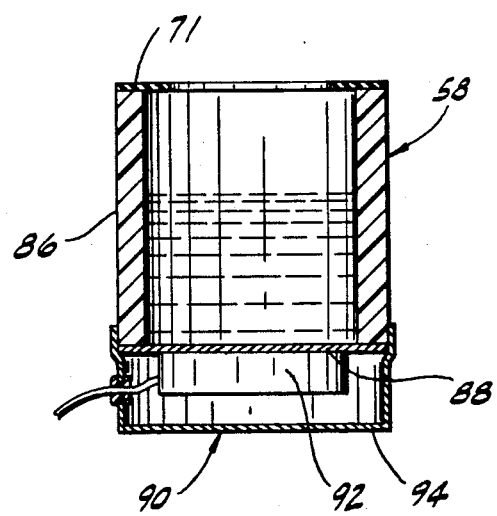
FIG. 11 is a longitudinal cross-sectional view of the cup shown in FIG. 10.

As shown in FIGS. 10 and 11, cup 58, like cup 16, includes a cylindrical sidewall 86 which is sealed at one end to bottom wall 88. Ultrasound applicator 90 includes a transducer 92 which is cemented or otherwise suitably affixed to the underside of bottom wall 88 and is protected by cap 94 which is slip fitted over the bottom of the cup.

Since ultrasound does not transmit through air, a coupling agent must be provided in cups 16 and 58 to provide coupling between the ultrasonic applicator and the testes to be treated. The particular coupling agent selected is preferably non-staining, non-irritating and slow evaporating. For this purpose, the agent may be water or water mixed with other materials. Other coupling agents such as oils or the like are also contemplated.

In use when the subject is ready for treatment, a cup is selected, filling with coupling agent and the patient is comfortably positioned so that his testicles are immersed therein. When chair 10 or stand 44 is used to hold the cup, this condition is readily accomplished by appropriate adjustments of the equipment to the patient as above described.

The length of the treatment, output frequency of the ultrasonic generator 100 coupled to ultrasound applicator 80 or 90 and power level at the applicator surface will vary in the individual case and is up to the treating physician. It has been found that generally the greater the energy applied to the testes, the more permanent is the suppression of spermatogenesis. Hence, the practical range of power depends upon the purpose of the treatment. Very high power levels, however, should be avoided to prevent burning the subject's skin. The most practical range is from about 0.25 to about 3 watt/cm$^2$ but the power level may go above or below that range. A preferred range is from about 0.5 to about 2 watt/cm$^2$ and a more preferred range is from about 0.5 to about 1 watt/cm$^2$.

Usually the frequency of the ultrasonic vibrations is within the range from about 500 to about 5000 KHZ. A preferred range is from about 500 to about 2500 KHZ and a particularly effective setting is 1100 KHZ ± 10 KHZ. Within the above mentioned ranges, the suppression of spermatogenesis tends to be more permanent with increasing frequency, other treatment variables remaining constant.

The length and number of treatments also has an effect on the degree that spermatogenesis is suppressed. Usually the treatment is within the range from about 3 to about 15 min., but by varying the other treatment conditions, the duration can be increased or shortened as desired.

It has been found that spermatogenesis can be suppressed by treatment at 1100 KHZ ± 10 KHZ with 1 watt/cm$^2$ for 10 min. The degree of suppression is determined by a sperm count. Since the normal count is about 50 to about 150 million/cc, a man with a count below about 20 million is regarded as infertile. If the subject's sperm count is too high after the first treatment, treatment as described above is repeated, however preferably after a wait of about 2 weeks. Again, a sperm count is taken and the treatment continued until the desired degree of suppression, either temporary or permanent, has been accomplished. The number of treatments to reduce the sperm count to zero for complete sterilization, if desired, depends upon the subject's condition, including such factors as his age and general health.

The following examples illustrate use of the apparatus described above.

EXAMPLE 1

A human patient with carcinoma of the prostate was selected and comfortably seated on chair 10. A cord (not shown) was loosely tied around the base of the scrotum to prevent displacement of the testes during treatment.

A cup 16 was selected of a size to accommodate the testicles of the subject. It was filled with water and the patient's testicles immersed therein. Cup 16 was then positioned by manipulation of bracket assembly 18 and drawer shelf 20 so that the testicles approached within ¼ to ½ inch of ultrasound applicator 80.

The transducer (not shown) in applicator 80 measured 11 cm² and was connected to an ultrasonic generator manufactured by Whitewater Electronics, Inc. This generator had a frequency of 1100 KHZ ± 10 KHZ, a continuous power output of 0 to 35 watts and was set so that the effective power level at applicator 80 was 1 watt/cm².

The patient's testes were treated with 1 watt/cm² of ultrasound for 10 minutes while he was seated on chair 10 as aforementioned.

Two weeks after treatment, the patient underwent orchiectomy and his testes were taken. Part of the testes were prepared for examination by light microscopy by immersing them in Bovin's solution for 48 hours. The testes were then transferred to 70% ethanol and embedded in paraplast. Four micron sections were cut, stained with hemotoxylin and eosin and examined under a light microscope.

Another part of the testes were prepared for examination by electron microscopy by cutting the seminiferous tubules into 3 mm lengths. The tubules were fixed first with 2% osmium tetroxide in 0.1 M phosphate buffer at pH 7.4 for 1 hour. This was followed by post-fixation in 3% glutaraldehyde in 0.1 M phosphate buffer at pH 7.4 for 1 hour.

The tubules were dehydrated with ethanol and embedded in Epon 812 according to standard procedure. When the blocks hardened, thin sections were stained with uranyl acetate for 15 min. followed by lead citrate for 5 min. These sections were examined under an electron microscope.

The results from light and electron microscopy showed that there were no sperm or spermatids in the tubules but that the Lyding cell population was normal. The blood testosterone level was also found to be normal.

EXAMPLE 2

A second human patient with carcinoma of the prostate was treated as described in Example 1 except that the ultrasonic generator was set so that the effective power level at applicator 80 was 0.5 watt/cm². Two weeks after treatment, the patient underwent orchiectomy and his testes were examined as in Example 1.

The results from light and electron microscopy showed that there were no sperm in the tubules and about a 50% reduction in the number of spermatid. The Lyding cell population was normal as was the blood testosterone level.

EXAMPLE 3

A third human patient with carcinoma of the prostate was treated as described in Example 1. Two days after treatment, the patient underwent orchiectomy and his testes were examined as in Example 1.

The results from light and electron microscopy showed that the membranes of the advanced testicular cells (spermatid and spermatocytes) had lost their integrity and exhibited very irregular shapes. Their plasma membranes had developed leaks and some cytoplasm had escaped into the interstitial area. The spermatogonia and sertoli cells, however, remained intact indicating that the destruction of sperm and spermatid was temporary and that the tubules were capable of spermatogenesis.

In view of the above, it will be seen that the several objects of the invention are achieved and other advantageous results attained.

As various changes could be made in the above described apparatus without departing from the scope of the invention, it is intended that all matters contained in the above description or shown in the accompanying drawings shall be interpreted as illustrative and not in a limiting sense.

What is claimed is:

1. A treatment device for a selected human male having a scrotum with testes comprising a vessel containing a coupling agent, an ultrasonic transducer means in operative relationship with said vessel to propagate continuous ultrasonic vibrations throughout the coupling agent, said vessel sized to receive and immerse in the coupling agent only the scrotum of the selected human male, ultrasonic generator means for generating continuous power to said transducer means to allow the transducer means to propagate said continuous vibrations, wherein said ultrasonic transducer means oscillate at a frequency between about 500 and about 5000 KHZ, support means for displacing the vessel vertically and maintaining the vessel in level condition while said scrotum is immersed in the coupling agent and said support means being further for displacing the vessel horizontally thereby adapting the vessel for alignment with the scrotum of the selected human male and for receipt and immersion of said scrotum.

2. The treatment device according to claim 1 wherein said ultrasonic transducer means oscillate at a frequency between about 500 and about 2500 KHZ.

3. The treatment device according to claim 2 wherein said ultrasonic transducer means have a power level between about 0.25 watt/cm² and about 3 watt/cm².

4. The treatment device according to claim 3 wherein said ultrasonic transducer means have a power level between about 0.5 watt/cm² and about 2 watt/cm².

5. The treatment device according to claim 4 wherein said ultrasonic transducer means have a power level between about 0.5 watt/cm² and about 1 watt/cm².

6. The treatment device according to claim 5 wherein said ultrasonic transducer means oscillate at a frequency of 1100 KHZ ± 10 KHZ.

7. The treatment device according to claim 1 which further comprises a chair having a seat and a front edge towards which the selected human male is faced when seated for treatment on the chair, said support means being mounted on said chair seat with the vessel adjacent the front edge of the chair.

8. The treatment device according to claim 7 wherein the chair has a back and a notch formed in the front edge of the chair, said notch aligned and freely accommodating the scrotum of the selected human male when seated on the chair for treatment, said notch extending substantially midway between the front edge of the chair and the back, said support means being mounted on an underside of the chair seat adjacent the notch.

9. The treatment device according to claim 1 and which further comprises a stand, the support means including an arm, said arm being mounted on said stand, said arm being vertically and horizontally adjustable on said stand.

* * * * *

UNITED STATES PATENT AND TRADEMARK OFFICE
CERTIFICATE OF CORRECTION

PATENT NO. : 4,078,556
DATED : March 14, 1978
INVENTOR(S) : Mostafa S. Fahim

It is certified that error appears in the above-identified patent and that said Letters Patent are hereby corrected as shown below:

Column 1, line 64, "microwavs" should read --microwaves--.

Column 2, line 9, "ben" should read --been--.

Column 3, line 24, "linkags" should read --linkages--.

Column 4, line 27, "filling" should read --filled--.

Column 4, line 42, "burning the" should read --burning of the--.

Column 6, claim 1, line 43, "500 and" should read --500 KHZ and--.

Column 6, claim 2, line 53, "500 and" should read --500 KHZ and--.

Signed and Sealed this

Twenty-ninth Day of August 1978

[SEAL]

Attest:

RUTH C. MASON
Attesting Officer

DONALD W. BANNER
Commissioner of Patents and Trademarks